(12) United States Patent
Ishizuka

(10) Patent No.: US 9,243,994 B1
(45) Date of Patent: Jan. 26, 2016

(54) MEASUREMENT DEVICE

(71) Applicant: YAMASHIN-FILTER CORP., Kanagawa (JP)

(72) Inventor: Masanori Ishizuka, Kanagawa (JP)

(73) Assignee: YAMASHIN-FILTER CORP., Kanagawa (JP)

( * ) Notice: Subject to any disclaimer, the term of this patent is extended or adjusted under 35 U.S.C. 154(b) by 0 days.

(21) Appl. No.: 14/823,996

(22) Filed: Aug. 11, 2015

(30) Foreign Application Priority Data

Aug. 21, 2014 (JP) ................... 2014-168214

(51) Int. Cl.
*G01N 21/00* (2006.01)
*G01N 15/14* (2006.01)

(52) U.S. Cl.
CPC ........ *G01N 15/1429* (2013.01); *G01N 15/1456* (2013.01)

(58) Field of Classification Search
CPC .............. G01N 21/53; G01N 15/0205; G01N 15/1459; G01N 21/51; G01N 15/1434
USPC ......................................................... 356/338
See application file for complete search history.

(56) References Cited

U.S. PATENT DOCUMENTS

| 4,270,041 A * | 5/1981 | Pleyber ................ G08B 23/00 377/19 |
| 5,394,732 A * | 3/1995 | Johnson .............. A61M 1/3626 73/19.03 |
| 8,402,815 B2 * | 3/2013 | Marra ................. B60H 1/008 73/28.04 |
| 2004/0145186 A1 * | 7/2004 | Inokuchi ............... B60L 11/123 290/40 C |
| 2011/0011186 A1 * | 1/2011 | Miyaji ................. G01F 1/74 73/61.356 |
| 2013/0171735 A1 * | 7/2013 | Lawson ................ B01J 8/001 436/55 |

FOREIGN PATENT DOCUMENTS

JP 2001-221793 A 8/2001

* cited by examiner

*Primary Examiner* — Tarifur Chowdhury
*Assistant Examiner* — Md Rahman
(74) *Attorney, Agent, or Firm* — Nakanishi IP Associates, LLC

(57) ABSTRACT

A measurement device includes: a light emitting section that continuously emits light into a liquid; a light receiving section that continuously receives the light continuously emitted from the light emitting section and that passed through the liquid, and converts the continuously received light into a continuous electrical signal; a particle detection section that amplifies by a first amplification ratio the continuous electrical signal converted by the light receiving section, and generates a particle detection signal as a continuous signal; an air bubble detection section that amplifies by a second amplification ratio that is smaller than the first amplification ratio the continuous electrical signal converted by the light receiving section, and generates an air bubble detection signal as a continuous signal; and a pollution level measurement section that generates a signal for measuring the pollution level of the liquid based on the particle detection signal and the air bubble detection signal.

3 Claims, 6 Drawing Sheets

MEASUREMENT DEVICE

CROSS-REFERENCE TO RELATED APPLICATIONS

This application claims priority from Japanese Patent Application No. 2014-168214 filed with the Japan Patent Office on Aug. 21, 2014, the entire content of which is hereby incorporated by reference.

BACKGROUND

1. Field of the Invention

The present invention relates to a measurement device.

2. Background Art

Japanese Unexamined Patent Application Publication No. 2001-221793A discloses a hydraulic oil pollution level diagnosis device in which when hydraulic oil is passed at a substantially constant velocity through a flow path within a microcell formed from a transparent glass material using a mini-pump, laser light emitted from light emitting devices provided at positions that sandwich the flow path from both the left and right sides passes through the hydraulic oil, and is received by light receiving devices provided at positions that sandwich the flow path from both the left and right sides, and a detection signal in accordance with the quantity of light received is output from the light receiving devices towards a controller.

As is disclosed in Japanese Unexamined Patent Application Publication No. 2001-221793A, if air bubbles or the like are contained in the hydraulic oil, the air bubbles are mistakenly detected as pollution, so there is a possibility that the state of pollution will not be correctly diagnosed.

SUMMARY OF THE INVENTION

One or more embodiments of the present invention provide a measurement device capable of simply measuring the pollution level, while preventing erroneous measurement due to air bubbles.

The measurement device according to one or more embodiments of the present invention includes: a light emitting section that continuously emits light into a liquid; a light receiving section that continuously receives the light continuously emitted from the light emitting section and that has passed through the liquid, and converts the continuously received light into a continuous electrical signal; a particle detection section that amplifies by a first amplification ratio the continuous electrical signal converted by the light receiving section, and generates a particle detection signal as a continuous signal; an air bubble detection section that amplifies by a second amplification ratio that is smaller than the first amplification ratio the continuous electrical signal converted by the light receiving section, and generates an air bubble detection signal as a continuous signal; and a pollution level measurement section that generates a signal for measuring the pollution level of the liquid based on the particle detection signal and the air bubble detection signal.

According to the measurement device of one or more embodiments of the present invention, a signal for measuring the pollution level of the liquid is generated based on a particle detection signal, which is a continuous signal generated by amplifying by a first amplification ratio a continuous electrical signal converted by the light receiving section, and an air bubble detection signal, which is a continuous signal generated by amplifying by a second amplification ratio that is smaller than the first amplification ratio the continuous electrical signal converted by the light receiving section. In this way, it is possible to simply measure the pollution level, while preventing erroneous measurement due to air bubbles.

Here, the air bubble detection section may output a signal that indicates that the pollution level cannot be measured when an integral value of the air bubble detection signal is equal to or greater than a threshold. In this way, the user can be informed that it is not possible to measure the pollution level due to the effect of air bubbles.

Here, the air bubble detection section outputs to the pollution level measurement section an air bubble suppression signal that takes a first value when the magnitude of the air bubble detection signal is not equal to or greater than the threshold, and takes a second value that indicates the occurrence of bubbles and that is greater than the first value when the magnitude of the air bubble detection signal is equal to or greater than the threshold. When the air bubble suppression signal takes the first value, the pollution level measurement section rectifies and integrates the particle detection signal and based on the result generates a pollution level measurement signal, and when the air bubble suppression signal takes the second value, the pollution level measurement section rectifies and integrates the signal from among the particle detection signal immediately prior to the air bubble suppression signal taking the second value, and based on the result generates the pollution level measurement signal. In this way, the effect of the air bubbles can be removed from the signal for measuring the pollution level of the liquid.

Here, the pollution level measurement section may determine the pollution level of the liquid based on the pollution level measurement signal, and output the determined result. In this way, the user can be informed of the pollution level of the liquid.

According to one or more embodiments of the present invention, it is possible to simply measure the pollution level, while preventing erroneous measurement due to air bubbles.

BRIEF DESCRIPTION OF THE DRAWINGS

FIG. 5A illustrates the case when the air bubble suppression signal S3 is 0 (V) (when an air bubble is not detected), and FIG. 5B illustrates a case in which the air bubble suppression signal S3 is $V_3$ (V) (when an air bubble is detected); FIG. 6A is an example of the display of the current stage of pollution level, and FIG. 5B is an example of a time series display of the pollution level at each predetermined time interval (for example, every 1 second).

DETAILED DESCRIPTION

Figure 1:
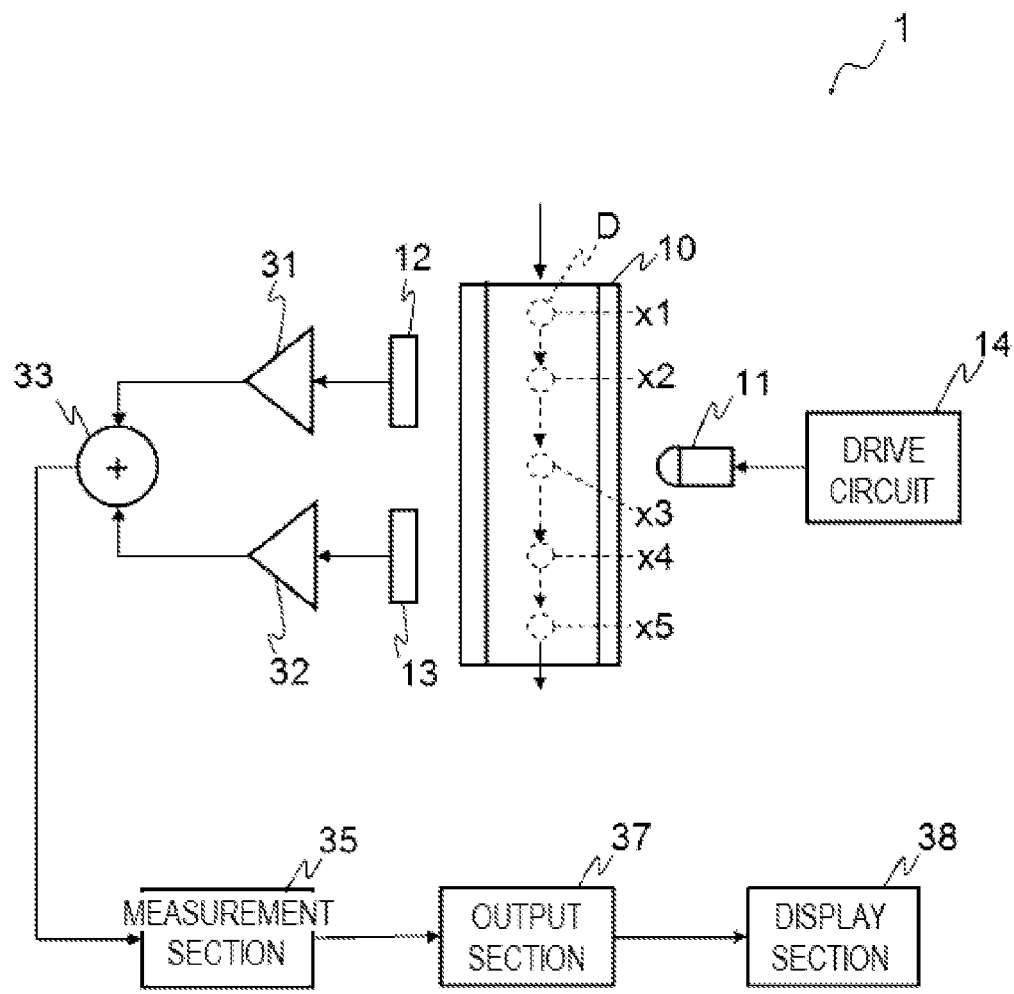
FIG. 1 schematically illustrates a pollution level measurement device 1 according to one example of the present invention.

Below, detailed description will be given of an embodiment of the present invention with reference to the drawings. FIG. 1 schematically illustrates a pollution level measurement device 1. The pollution level measurement device 1 is provided at an appropriate position on a device for carrying out required operations using a liquid, such as construction machinery, hydraulic equipment, and the like.

At least a portion of a measurement flow path 10 through which flows a liquid such as oil, water, or the like that is the subject of the measurement is formed from a transparent material. In other words, the entire measurement flow path 10 may be formed from a transparent material, or windows for introducing light and for extracting light may be formed in a portion thereof.

A light emitting section (for example, an LED) 11 for irradiating light into the measurement flow path 10 from one side face thereof is disposed in the portion of the measurement flow path 10 formed from the transparent material. Light receiving devices 12, 13 for detecting the transmitted light of the irradiated light are provided on the opposite side to the light emitting section 11, sandwiching the measurement flow path 10. The light receiving devices 12, 13 are, for example, photodiodes (PD), and are arranged separated from each other at a predetermined distance along the flow path direction of the measurement flow path 10.

The light emitting section 11 is driven by a drive circuit 14. The drive circuit 14 includes a constant current circuit or the like so that the quantity of light emitted by the light emitting section 11 is constant. In the present embodiment, light is continuously emitted from the light emitting section 11. Also, the light receiving devices 12, 13 continuously receive light. The drive circuit 14 may also include an APC circuit that feeds back the quantity of light received by the light receiving devices 12, 13.

The output signal of the light receiving device 12 is amplified by an amplifier 31, and input to an adder-subtractor 33, and the output signal of the light receiving device 13 is amplified by an amplifier 32, and input to the adder-subtractor 33. Then, the differential output of the light receiving devices 12, 13 is obtained from the adder-subtractor 33. The output signals from the light receiving device 12 and the light receiving device 13 are continuous signals, so the differential output of the light receiving device 12 and the light receiving device 13 is also a continuous signal. Then the quantity of particles included in the liquid flowing within the measurement flow path 10 is measured based on the differential output of the light receiving devices 12, 13.

When there are no impurity particles such as a particle D or the like, the differential output is 0 if the same quantity of light is received by the light receiving devices 12, 13. For example, when a particle D flows in the flow path from the position x1 towards the position x5, when the particle D is at the position x1, the quantity of light received by the light receiving devices 12, 13 is the same so the differential output is 0.

When the particle D is at the position x2, the quantity of light received by the light receiving device 12 is less than that of the light receiving device 13 by the amount of light shielded by the particle D, so the differential output has a negative value. When the particle D comes to the position x3, the quantity of light received by the light receiving devices 12, 13 becomes the same again, and the differential output is 0. When the particle D comes to the position x4, the quantity of light received by the light receiving device 13 becomes shielded by the impurity and the differential output has a positive value, the opposite to the case where the particle D is at the position x2. Then, when the particle D passes through the light path and comes to the position x5, the quantity of light received by the light receiving devices 12, 13 becomes the same and the differential output becomes 0.

Figure 2:
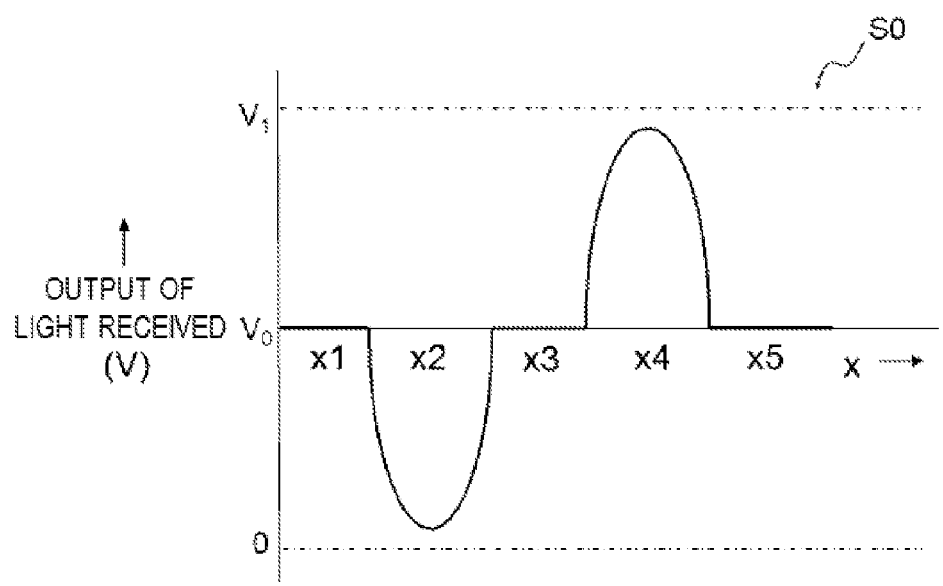
FIG. 2 illustrates one example of a differential output signal wave form.

FIG. 2 illustrates the wave form of the differential output signal SO when the particle D flows through the flow path from the position x1 towards the position x5. The differential output signal SO is a signal that can take values between 0 to V1 (V), with V0 (V) as center. V0 is any value equal to or greater than 0. Also, V1 is about double V0. The wave height value in the differential output signal SO is proportional to the size of the particle D. Also, the spacing between the two wave forms corresponds to the time for passage between the light receiving devices 12, 13.

In this way, by the particle D shielding the light path to the two light receiving devices 12, 13 one at a time, the differential output signal SO is output as a wave form having positive and negative values, and the number of wave forms increases in proportion to the quantity of particles D. In the differential output signal SO, the frequency components include a component related to the flow velocity, and the average value or effective value includes a component related to the density.

Note that in the present embodiment, the differential output of the light receiving devices 12, 13 is used, but this is to increase the variation in the quantity of light due to the particles such as the particle D or the like, without increasing the output from the light emitting section 11. However, if the quantity of particles is too large, it becomes difficult to obtain a difference in the quantity of light entering the light receiving devices 12, 13. Also, if the quantity of particles is small, the spacing between the wave forms detected becomes large. Therefore, preferably the spacing between the light emitting device—the flow path—the light receiving devices, the spacing between the two light receiving devices, and the optical system such as the light receiving area of the light receiving devices and the like are appropriately varied in accordance with the size or quantity (density) of the particles to be detected, so that the number of wave forms has a monotonically increasing relationship to the number of particles.

Returning to the description of FIG. 1. The output from the adder-subtractor 33 is input to a measurement section 35. The measurement section 35 is connected to an output section 37. A display, a processing device, a memory device, a communication apparatus, a construction machine, or the like is connected to the output section 37. The measurement result is displayed on the display, stored in the memory device, output to the construction machine via the communication apparatus, and displayed in the construction machine. In the present embodiment, a display section 38 is connected to the output section 37.

When the quantity of particles is detected as the volume ratio included in the fluid, the differential output signal can be rectified (half-wave/full-wave) as shown in FIG. 2, and by passing it through an integration circuit that is sufficiently delayed with respect to the frequency components of the wave form of the differential output signal (it is also possible to obtain a moving average or the like after A/D conversion), an integrated signal having a monotonically increasing relationship with respect to the quantity of particles can be obtained. The integrated value can be considered to be the differential output signal from which the flow velocity component is removed, and only the average value or effective value, which is the density component, is extracted.

However, when air bubbles or the like are included in the fluid, the differential output signal from the two light receiving devices 12, 13 includes the effect of the air bubbles. In the differential output signal, air bubbles are output as a larger signal than the particles. It is a feature of the present embodiment that the effect of air bubbles is removed from the differential output signal. The following is a detailed description of this feature of the present embodiment.

Figure 3:
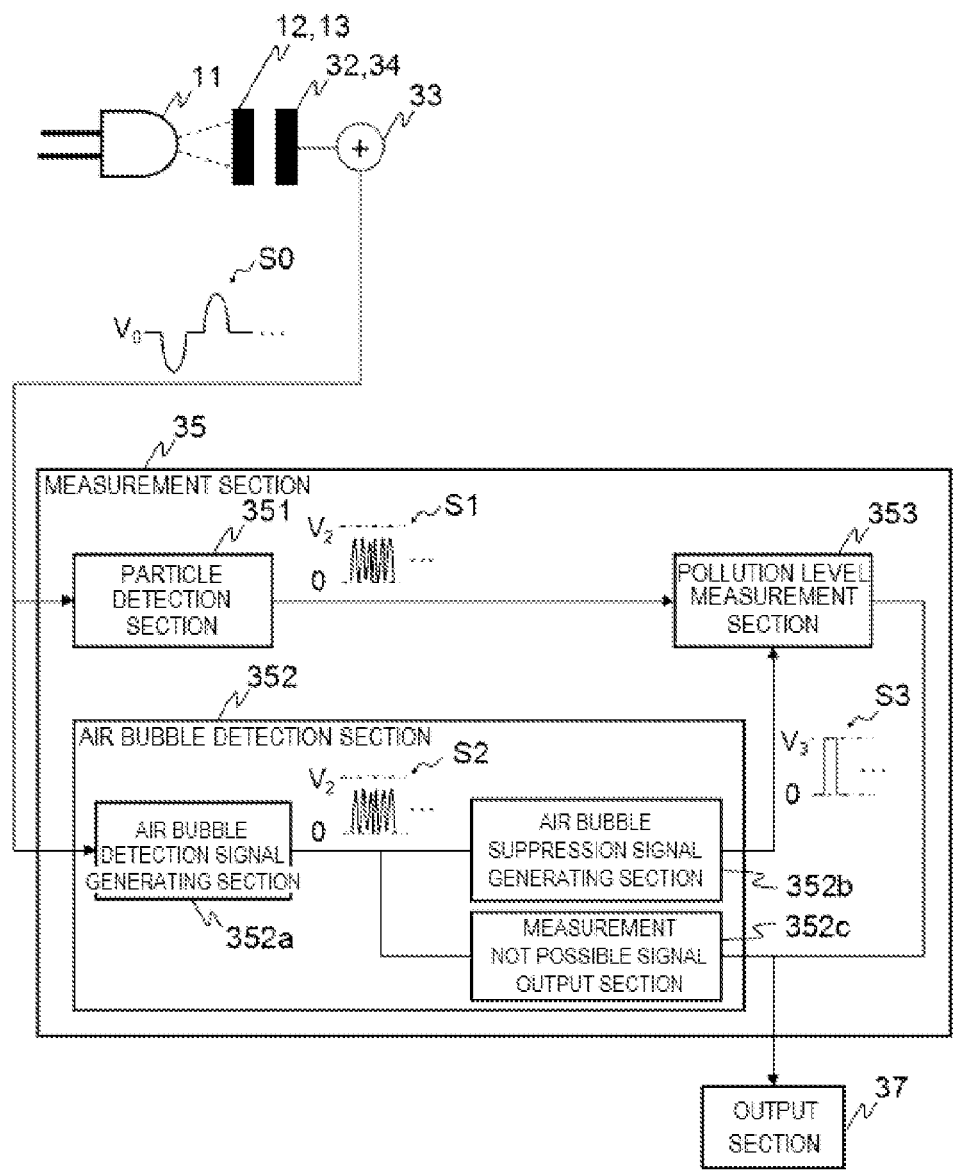
FIG. 3 is a block diagram illustrating an example of the electrical configuration of a measurement section 35.

FIG. 3 is a block diagram illustrating an example of the electrical configuration of the measurement section 35. The measurement section 35 removes the effect of the air bubbles from the differential output signal, and the quantity of particles D included in the liquid, in other words the pollution level, is detected based on the signal after removing the effect of the air bubbles. Note that in FIG. 3 the lines connecting each of the components schematically illustrates the flow of signal.

The measurement section 35 mainly includes a particle detection section 351, an air bubble detection section 352, and a pollution level measurement section 353.

The particle detection section 351 obtains the differential output signal SO output from the adder-subtractor 33. Also, the particle detection section 351 amplifies the differential output signal SO by a first amplification ratio A1, carries out full-wave rectification, and generates a particle detection signal S1. The particle detection signal S1 is a signal having a value from 0 to $V_2$ (V), where $V_2$ is any value equal to or greater than 0 (V). The differential output signal SO is a continuous signal, so the particle detection signal S1 is also a continuous signal. In the present embodiment, the first amplification ratio A1 is about 400 to 450.

The air bubble detection section 352 mainly includes an air bubble detection signal generating section 352a, an air bubble suppression signal generating section 352b, and a measurement not possible signal output section 352c.

The air bubble detection signal generating section 352a obtains the differential output signal SO output from the adder-subtractor 33. Also, the air bubble detection signal generating section 352a amplifies the differential output signal SO by a second amplification ratio A2, carries out full-wave rectification, and generates an air bubble detection signal S2. The air bubble detection signal S2 is a signal having a value from 0 to $V_2$ (V), where $V_2$ is any value equal to or greater than 0 (V). The differential output signal SO is a continuous signal, so the air bubble detection signal S2 is also a continuous signal. In the present embodiment, the second amplification ratio A2 is about 30 to 45.

When an air bubble is detected, the crest value of the differential output signal SO is a larger value compared with when a particle is detected. Therefore, the air bubble detection signal S2 is generated by amplification by the second amplification ratio A2 that is smaller than the first amplification ratio A1, so that the particles are not detected and only the air bubbles can be detected (the maximum value of the air bubble detection results is a value close to $V_2$ (V). As a result, in the air bubble detection signal S2, the results of detection of particles do not appear as a wave form, and only the results of detection of air bubbles appear as a wave form. Note that in the present embodiment, the first amplification ratio A1 is set to about 10 times the second amplification ratio A2, but the first amplification ratio A1 and the second amplification ratio A2 are not limited to this.

The air bubble suppression signal generating section 352b obtains the air bubble detection signal S2 from the air bubble detection signal generating section 352a. Also, the air bubble suppression signal generating section 352b generates an air bubble suppression signal S3 based on the air bubble detection signal S2. The following is a description of the process of generating the air bubble suppression signal S3.

Figure 4:
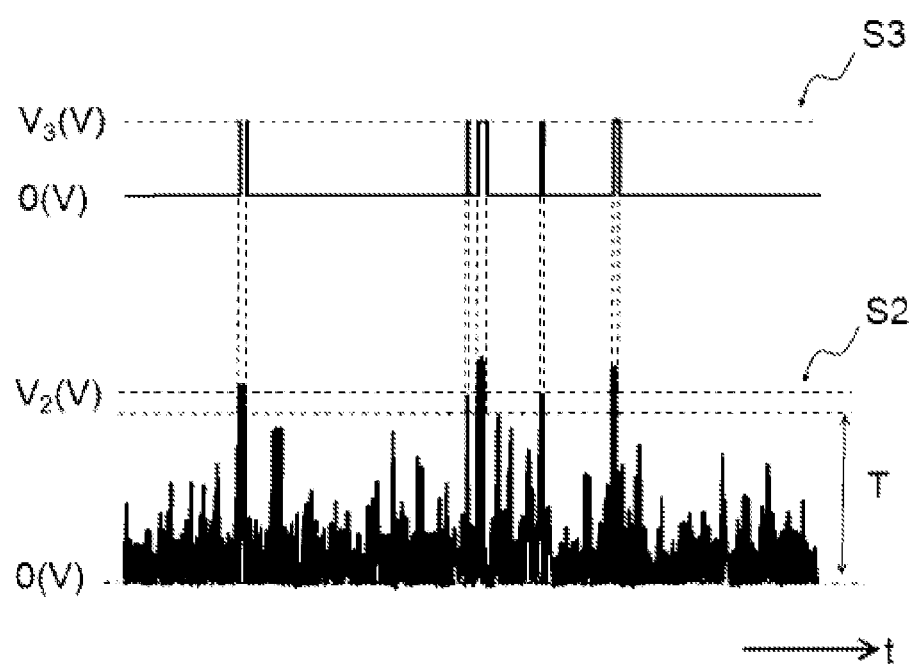
FIG. 4 illustrates an air bubble detection signal S2 and an air bubble suppression signal S3.

FIG. 4 illustrates the air bubble detection signal S2 and the air bubble suppression signal S3. The air bubble detection signal S2 is a signal after rectification, so it is a signal having a plurality of wave forms that project in the positive direction from 0 (V). The air bubble suppression signal S3 is a signal that includes two values: 0 (V) (Low), and $V_3$ (V) (High). In the present embodiment, $V_3$ (V) is +5 (V), but the value of $V_3$ (V) is not limited to this provided it is a value larger than 0 (V).

If an air bubble is not detected, in other words if the value of the air bubble detection signal S2 is not equal to or greater than a threshold T, the air bubble suppression signal generating section 352b generates a 0 (V) (Low) signal as the air bubble suppression signal S3. Also, when the value of the air bubble detection signal S2 is equal to or greater than the threshold T, the air bubble suppression signal generating section 352b generates the $V_3$ (V) (High) signal as the air bubble suppression signal S3, as an air bubble has been detected.

The threshold T is set to a voltage value between 0 and $V_2$ (V). The accuracy of detection of air bubbles can be changed by changing the magnitude of the threshold T. For example, if the threshold T is reduced the air bubble detection accuracy increases, and if the threshold T is increased the air bubble detection accuracy is reduced.

In the present embodiment, when the air bubble suppression signal S3 is generated, the differential output signal SO is amplified by the second amplification ratio A2, full-wave rectification is carried out, and the generated air bubble detection signal S2 is compared with the threshold T. However the differential output signal SO that has been amplified by the second amplification ratio A2 (signal that has not been rectified) may also be compared with the threshold T. In this case, the amplitude of the signal in the positive and negative directions from the central value may be compared with the threshold T.

Returning to the description of FIG. 3. If the air bubble detection quantity, detection frequency, and the like based on the air bubble detection signal S2 is equal to or greater than a certain value, the measurement not possible signal output section 352c outputs a measurement not possible signal that indicates that it is not possible to measure the pollution level. Specifically, if an integral value of the air bubble detection signal S2 (the signal that is the basis for outputting the measurement not possible signal) is equal to or greater than a predetermined value (that can be set as desired), in other words if the quantity of air bubbles is equal to or greater than a predetermined quantity, the measurement not possible signal output section 352c outputs the measurement not possible signal. Note that the measurement not possible signal may be in any form.

In the present embodiment, the measurement not possible signal output section 352c obtains the integral value of the air bubble detection signal S2 using an RC circuit (integrating circuit). If an air bubble detection signal S2 having positive values is continuously input to the RC circuit, the integral value of the air bubble detection signal S2 is smoothed and the value gradually increases. Also, if the value of the air bubble detection signal S2 input to the RC circuit is 0 (V) or small, the integral value of the air bubble detection signal S2 becomes gradually smaller, and ultimately equals 0 (V). In this way, by using the RC circuit (integrating circuit), the integral value of the air bubble detection signal S2 varies gently, which prevents the measurement not possible signal from being frequently output, and measurement being not possible.

Also, a microcomputer can be used for obtaining the integral value of the air bubble detection signal S2. When a microcomputer is used, the air bubble detection signal S2 may be integrated continuously for a fixed period of time (for example 1 second), and reset every fixed period of time. Also, if the integral value within the fixed period of time is equal to or greater than a predetermined value, the measurement not possible signal may be output.

Note that the method of obtaining the detection quantity or detection frequency of air bubbles is not limited to the method of obtaining the integral value of the air bubble detection signal S2.

The measurement not possible signal output section 352c outputs the measurement not possible signal to the output section 37. When the measurement not possible signal is obtained, the output section 37 outputs an error signal to the display section 38, for example a display device such as a liquid crystal display, a light emitting section such as an LED, or the like. For example, when a display device is used as the display section 38, the output section 37 outputs character information such as "Measurement is not possible" or the like to the display section 38 as an error signal. Also, when for example a light emitting section is used as the display section 38, the output section 37 outputs to the display section 38 a blinking signal to cause the light emitting section to blink, as the error signal. In this way, the user can be informed that it is not possible to measure the pollution level due to the effect of air bubbles.

Note that the display section 38 may be a device provided by the pollution level measurement device 1, or it may be provided separately from the pollution level measurement device 1. Also, the output section 37 may be included in the measurement section 35.

The pollution level measurement section 353 obtains the particle detection signal S1 from the particle detection section 351, and obtains the air bubble suppression signal S3 from the air bubble suppression signal generating section 352b. The pollution level measurement section 353 processes the particle detection signal S1 based on the particle detection signal S1 and the air bubble suppression signal S3, and generates a pollution level measurement signal that is the particle detection signal S1 from which the effect of the air bubbles has been removed. The following is a specific description of the process performed by the pollution level measurement section 353.

Figure 5A:
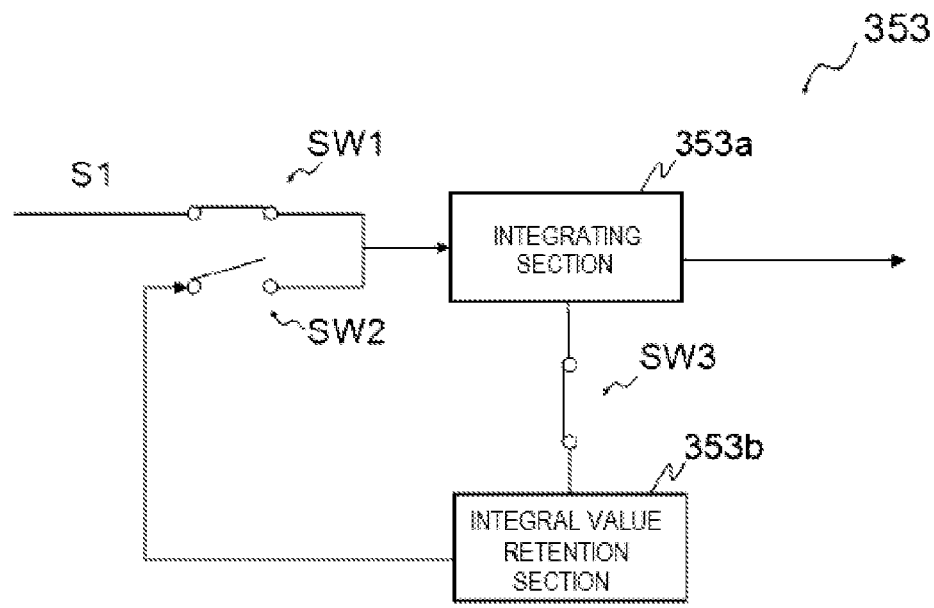
FIGS. 5A and 5B schematically illustrate the processing carried out by a pollution level measurement section 353.
Figure 5B:
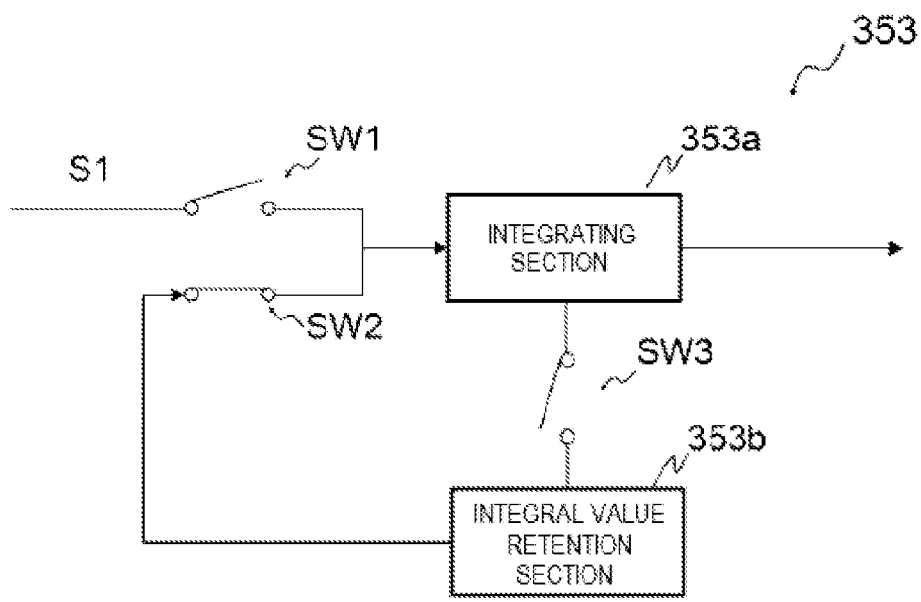

FIGS. 5A and 5B schematically illustrate the process carried out by the pollution level measurement section 353. FIG. 5A illustrates the case when the air bubble suppression signal S3 is 0 (V) (when an air bubble is not detected), and FIG. 5B illustrates the case in which the air bubble suppression signal S3 is $V_3$ (V) (when an air bubble is detected).

The pollution level measurement section 353 mainly includes an integrating section 353a, an integral value retention section 353b, and switches SW1, SW2, SW3. When the air bubble suppression signal S3 is 0 (V), the pollution level measurement section 353 closes the switch SW1 and the switch SW3, and opens the switch SW2. Also, when the air bubble suppression signal S3 is $V_3$ (V), the pollution level measurement section 353 closes the switch SW2 and opens the switch SW1 and the switch SW3.

The integrating section 353a calculates the integral value by integrating the input signal, and outputs the integral value as a pollution level measurement signal. A commonly known integrating circuit or the like can be used as the integrating section 353a. Note that the integrating section 353a may amplify the integral value as the pollution level measurement signal.

Also, the integrating section 353a outputs the calculated integral value to the integral value retention section 353b. The integral value retention section 353b retains the integral value most recently input from the integrating section 353a until the next integral value is input from the integrating section 353a. A commonly known holding circuit or the like can be used as the integral value retention section 353b.

When the air bubble suppression signal S3 is 0 (V), the particle detection signal S1 is input to the integrating section 353a, and the pollution level measurement signal obtained by integrating the particle detection signal S1 is output from the integrating section 353a, as illustrated in FIG. 5A.

In contrast, when the air bubble suppression signal S3 is $V_3$ (V), because the switch SW1 is open and the switch SW2 is closed as illustrated in FIG. 5B, the particle detection signal S1 is not input to the integrating section 353a, and the integral value output from the integral value retention section 353b is input to the integrating section 353a. At this time, because the switch SW3 is open, the integral value output from the integral value retention section 353b is the integral value obtained by integrating the particle detection signal S1 immediately before the air bubble suppression signal S3 became $V_3$ (V). As a result, the integrating section 353a outputs the pollution level measurement signal obtained by integrating the value obtained by integrating the particle detection signal S1 immediately before the air bubble suppression signal S3 became $V_3$ (V).

In this way, the pollution level measurement section 353 can generate the pollution level measurement signal that excludes the effect of the air bubbles. However, the method of generating the pollution level measurement signal that excludes the effect of the air bubbles is not limited to this.

Also, the pollution level measurement section 353 determines the pollution level of the liquid such as oil or water that is the object of the measurement, based on the pollution level measurement signal output from the integrating section 353a. For example, the pollution level measurement section 353 determines the pollution level based on the value of the pollution level measurement signal using an evaluation method such as the NAS class method, or the ISO contamination code. Then, the pollution level measurement section 353 outputs the determined level of pollution to the output section 37. The output section 37 outputs the pollution level output from the pollution level measurement section 353 to the display section 38, for example as a display device such as a liquid crystal display, or a light emitting section such as an LED.

Figure 6A:
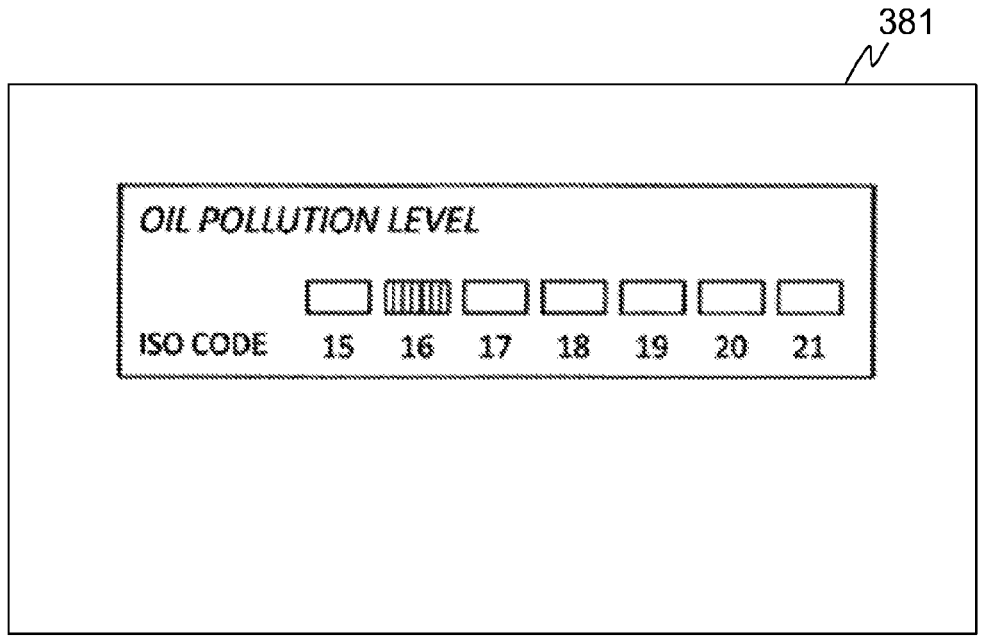
FIGS. 6A and 6B illustrate an example of the display of the pollution level by the display section 38.
Figure 6B:
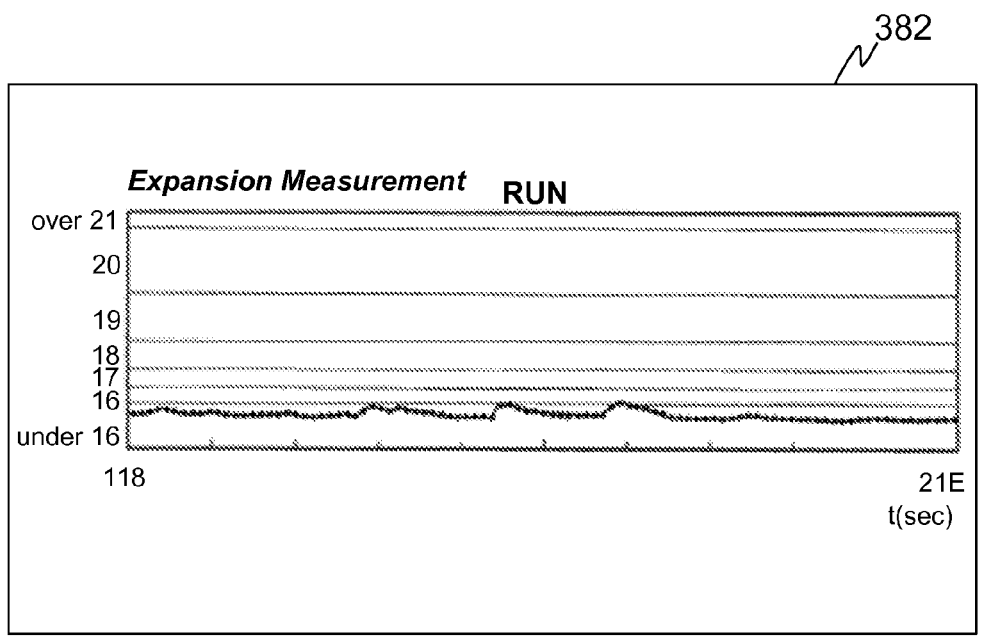

FIGS. 6A and 6B illustrate an example of the pollution level displayed in the display section 38, using a display device as the display section 38. In the example illustrated in FIG. 6A, the pollution level at the present stage is displayed in a display region 381 of the display section 38. In the example illustrated in FIG. 6B, the pollution level is displayed as a time series at a predetermined period of time (for example, every 1 second) in a display region 382 of the display section 38. The pollution level is indicated as a numerical value that indicates the pollution level that is divided into a plurality of stages. In FIGS. 6A and 6B, the pollution level is indicated using an ISO code, but this is not a limitation. In this way, the user can be informed of the pollution level. Note that the present embodiment is not limited to that illustrated on the drawings.

Note that in the present embodiment, the pollution level measurement section 353 outputs the result of determining the pollution level to the output section 37, but the signal output by the pollution level measurement section 353 to the output section 37 is not limited to this. For example, the pollution level measurement section 353 may output the pollution level measurement signal to the output section 37, or may determine whether or not the pollution level of the liquid is equal to or greater than a fixed level, and output the result to the output section 37.

When the pollution level measurement signal is output to the output section 37, the output section 37 outputs the pollution level measurement signal to the display section 38, an external processing device, or the like. When the pollution level measurement signal is output to the display section 38, the display section 38 displays the pollution level measurement signal as it is. When the pollution level measurement signal is output to an external processing device or the like, the processing device or the like may determine the pollution level by the NAS class method, the ISO contamination code value, or the like based on the pollution level measurement signal, and notify the user. Alternately the processing device or the like may determine whether the pollution level exceeds a predetermined threshold (determine whether or not the pollution level of the liquid is equal to or greater than a specific level), and notify the user, or may determine a limit of operation of a constituent element of a device on which the pollution level measurement device 1 is provided, and notify the user.

For example, when the pollution level measurement section 353 or an external processing device or the like outputs that the pollution level of the liquid is equal to or greater than a specific level, the output section 37 may output to the display section 38, which is a display, character information such as "The oil is polluted. Please change . . . " as a warning signal, or may output to the display section 38, which is a light emitting section, a signal to turn on the light emitting section.

According to the present embodiment, it is possible to correctly measure the pollution level with the effect of air bubbles removed, by preventing erroneous measurement due to air bubbles.

Also, according to the present embodiment, the measurement device is compact with a simple structure, so by just installing the measurement device on equipment that performs a desired operation using the liquid, the pollution level can be simply measured. Also, by constantly installing the measurement device on equipment that performs a desired operation using the liquid, the pollution level can be constantly monitored.

Note that in the present embodiment, the measurement section 35 outputs various signals such as the pollution level of the liquid or the measurement not possible signal, and the output section 37 outputs the various signals to the display section 38. However, the output section 37 may output the various signals to an external output device or the like via a network (either cable or wireless).

Also, in the present embodiment, the pollution level measurement device 1 uses a transmission type light detection device, but the light detection device used in the pollution level measurement device 1 is not limited to a transmission type, and various forms of light detection device can be used such as a reflection type or a light scattering type. Also, an analog circuit may be used as the measurement section 35, or a digital circuit that includes a microcomputer or the like may be used.

Embodiments of the invention have been described in detail with reference to the drawings; however, specific configurations are not limited to the embodiments, and changes in the design or the like are also included in a range which does not depart from the gist of the invention. For example, the above examples have been explained in detail in order to facilitate understanding of the present invention and are not necessarily limited to examples provided with the entirety of the configuration described above. Also, a part of the configuration of one embodiment can be replaced with the configuration of another embodiment, and, another configuration can be added, deleted, or replaced on the configuration of an embodiment. Also, in the present invention, "substantially" is a concept that includes variation or modification to the extent that sameness is not lost, and does not only mean strictly the same.

What is claimed is:

1. A measurement device, comprising:
   a light source configured to continuously emit light into a liquid;
   a light receiving device configured to continuously receive the light continuously emitted from the light emitting section and that has passed through the liquid, and converts the continuously received light into a continuous electrical signal; and
   a microcomputer or electric circuit(s) configured to:
   amplify by a first amplification ratio the continuous electrical signal converted by the light receiving section, and generates a particle detection signal as a continuous signal;
   amplify by a second amplification ratio that is smaller than the first amplification ratio the continuous electrical signal converted by the light receiving section, and generates an air bubble detection signal as a continuous signal; and
   generate a signal for measuring the pollution level of the liquid based on the particle detection signal and the air bubble detection signal,
   wherein:
   the microcomputer or electric circuit(s) output to the pollution level measurement section an air bubble suppression signal that takes a first value when a magnitude of the air bubble detection signal is not equal to or greater than a threshold, and takes a second value that indicates the occurrence of bubbles and that is greater than the first value when the magnitude of the air bubble detection signal is equal to or greater than the threshold; and
   when the air bubble suppression signal takes the first value, the microcomputer or electric circuit(s) rectify and integrates the particle detection signal and based on the result generates a pollution level measurement signal; and
   when the air bubble suppression signal takes the second value, the microcomputer or electric circuit(s) rectify and integrates the signal from among the particle detection signal immediately prior to the air bubble suppression signal taking the second value, and based on the result generates the pollution level measurement signal.

2. The measurement device according to claim 1, wherein the microcomputer or electric circuit(s) output a signal that indicates that the pollution level cannot be measured when an integral value of the air bubble detection signal is equal to or greater than the threshold.

3. The measurement device according to claim 1, wherein the microcomputer or electric circuit(s) determine the pollution level of the liquid based on the pollution level measurement signal, and outputs the determined result.

\* \* \* \* \*